US00PP11524P

United States Patent [19]

Twomey

[11] Patent Number: Plant 11,524

[45] Date of Patent: Sep. 26, 2000

[54] HYBRID TEA ROSE PLANT NAMED 'TWOJOAN'

[76] Inventor: Jerry F. Twomey, 194 Avocado St., Leucadia, Calif. 92024

[21] Appl. No.: 09/220,900

[22] Filed: Dec. 24, 1998

[51] Int. Cl.[7] ..... A01H 5/00

[52] U.S. Cl. ..... Plt./138

[58] Field of Search ..... Plt./139, 138, 137, Plt./130

*Primary Examiner*—Howard J. Locker

[57] ABSTRACT

A new rose cultivar of the Hybrid Tea class characterized by having large pink flowers on a very vigorous, healthy plant with very glossy foliage. This plant has been designated as 'TWOJOAN'. It is being marketed in the USA under the tradename of 'Dream Pink'.

1 Drawing Sheet

The present invention relates to a new and distinctive cultivar of rose plant of the Hybrid Tea class, which was originated by my crossing 'White Masterpiece' as the seed parent with the pollen parent 'Silver Jubilee'.

Among the novel characteristics possessed by the new cultivar which distinguish it from:

(a) All other cultivars of which I am aware are: (1) Very large pink flowers. (2) Intense fruity fragrance. (3) Distinctive glossy foliage with very serrated edges. (4) Tall vigorous healthy bush.

(b)

*Seed parent.*—Large white HT.

*Pollen parent.*—Two-tone light pink HT.

Asexual reproduction of the new rose cultivar by budding, as performed at Wasco, Calif. shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horitcultural Society Colour Chart.

Parentage:

*Seed parent.*—'White Mastepiece', U.S. Plant Pat. No. 2,998.

*Pollen parent.*—'Silver Jubilee', not patented.

Class: Hybrid Tea

The following observations are made of specimens grown outdoors in Monterey County, Calif., in the month of September.

FLOWER

Blooming habit:

A. Bud:

(1) *Size.*—Sepals enclosed, 2.5 cm from base of sepals to top of bud.

(2) *Form.*—Ovoid.

(3) *Sepals.*—5–7 cm in length; 1½–2 cm extension beyond bud; no serration shown on sepal edges. Generally 3 out of 5 sepals show appendages on each side, 4 to 7 mm length. Sepals show heavy glandular development on edges. Light cotton matting on inner surface; fine hairs with some glandular development on outer surface. Outside color — 183B; inside — 139C.

(4) *Peduncle.*—Length — 6–7 cm. Surface smooth with some glandular hairs. Strength — firm; Color — 144A with shadings of 183B.

(5) *Receptacle.*—Shape-round, 10–12 mm diameter. Color same as peduncle.

(6) *Color.*—When sepals first divide, outside bud petals near to 54A.

B. Bloom:

(1) *Size.*—When open: 12–13 cm.

(2) *Borne.*—1 per stem.

(3) *Form.*—Urn shaped.

(4) *Petalage.*—Average — 20 to 22.

(5) *Color.*—Early open: outer petals near 54A; inner petals near 55B. Aging: Lightening to 55C om both sides.

C. Petals:

(1) *Texture.*—Firm.

(2) *Appearance.*—Satiny.

(3) *Form.*—Smooth, even edge.

(4) *Arrangement.*—Regular.

(5) *Petaloids in center.*—Average 2–3.

(6) *Persistence.*—Heavy substance, long lasting.

(7) *Fragrance.*—Heavy strong fruit.

(8) *Lasting quality.*—On plant 6–8 days; cut 8 days.

REPRODUCTIVE ORGANS

A. Stamen:

(1) *Arrangement.*—Even.

(2) *Number.*—Average 170–180.

(3) *Length.*—Average — 5 to 12 mm.

(4) *Filaments.*—Color — Close to 4D.

(5) *Anthers.*—Color — Close to 22A.

(6) *Pollen.*—Close to 21C.

B. Pistil:

(1) *Styles.*—Length: 10–18 mm crossection extending from ovary wall; number; 105–115; color: near to 4D; sparsely coated with white hairs.

(2) *Stigma.*—Color — Color to 4C.

(3) *Ovary.*—Shape — round; center crossection at sepal base: 8–9 mm.

C. Hips:
*Diameter.*—22–24 mm.
*Color.*—53B with shadings of 43A;
*Average number of seed.*—10.

PLANT

A. Form: Upright.
B. Growth: Vigorous, Height: average 1–1.25 m.
C. Stem length: Basal break to flower bud tip: average 1–1.25 m.
D. Foliage: Compound of 3 to 5 leaflets on bloom stem; 5 to 7 leaflets on main canes.
(1) *Mature size.*—tip of leaflet to stipule base 13–15 cm.
(2) *Quantity.*—Stems well covered.
(3) *Color.*—New foliage upper and lower side close to 147B with shadings of 183A. Old foliage upper side near to 147A, under side near to 147A with shadings of 183A.
(4) *Shape.*—Oval with center pointed.
(5) *Texture.*—Firm, very leathery.
(6) *Edge.*—Notable serration on outer edge. Average 4 points per 1 cm, with 1–2 mm peak.
(7) *Rachis.*—Glandular hair on upper and lower side. Prickles on lower side: 2–3 mm length; hooked; spacing 10–12 mm apart.
(8) *Stipules.*—Length 18–20 mm; auricle to 5–6 mm. Edge of stipule to tip of auricle with many glandular hairs.
E. Resistance to disease: Powdery mildew, rust amd black-spot — Very good.
F. Wood:
*New wood.*—Color close to 146B.
*Old Wood.*—Color close to 147B with shadings of 178B.
G. Thorns on mature wood:
*Size.*—8–10 mm.
*Number per* 10 *cm.*—Mature wood — 6 thorns.
*Shape.*—Downward curvature.
*Color.*—Early stage close to 166B; Aging close to 166A.
H. Winter hardiness: Good.

I claim:

1. A new and distinct rose cultivar of the hybrid tea class, substantially as herein shown and described.

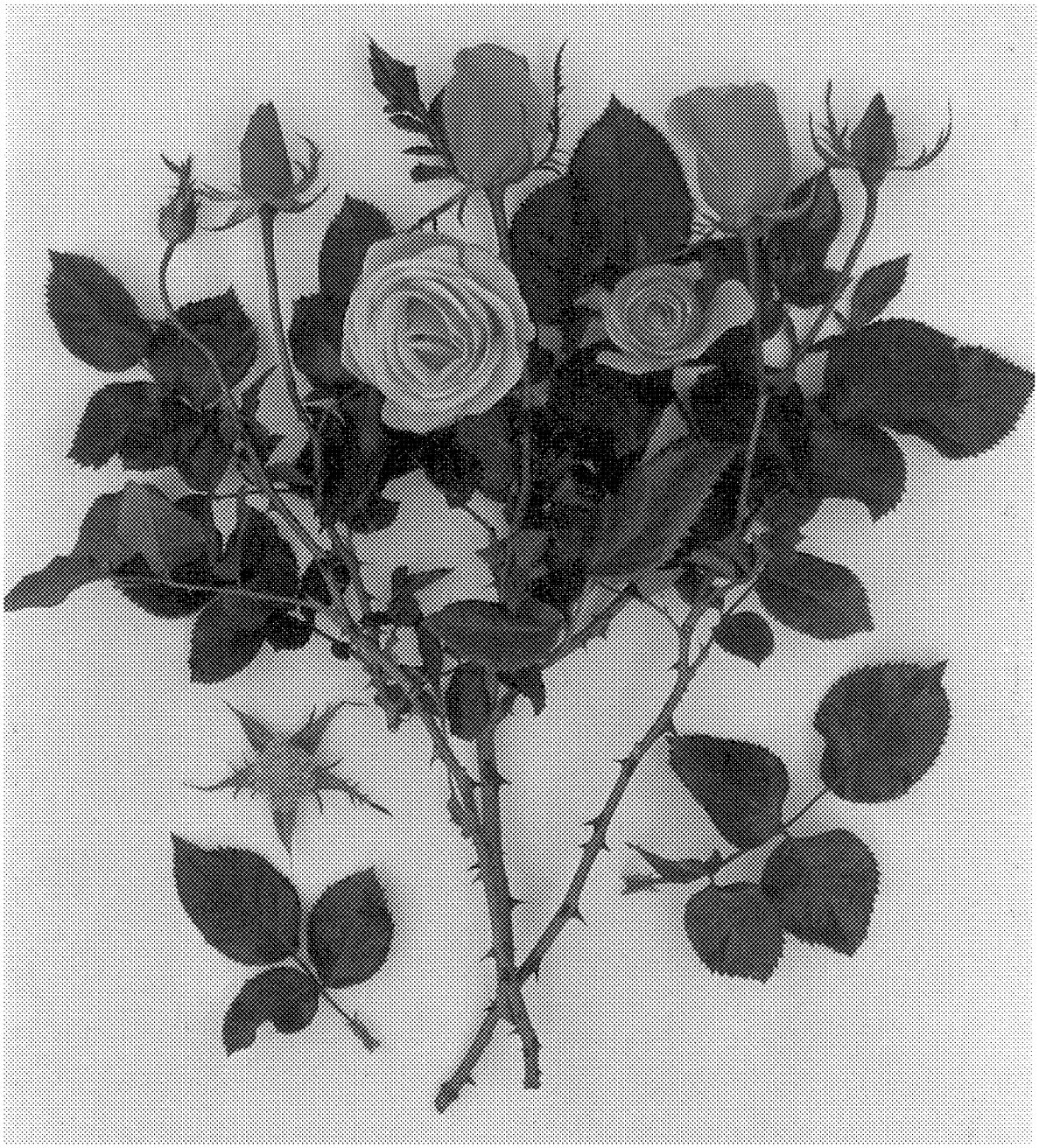

* * * * *